(12) United States Patent
Fischer et al.

(10) Patent No.: US 7,074,582 B2
(45) Date of Patent: Jul. 11, 2006

(54) METHOD FOR ASSESSING COAGULATION

(75) Inventors: Timothy J. Fischer, Oro Valley, AZ (US); Trevor Baglin, Cambridge (GB); Liliana Tejidor, Raleigh, NC (US)

(73) Assignee: bioMerieux, Inc., Durham, NC (US)

( * ) Notice: Subject to any disclaimer, the term of this patent is extended or adjusted under 35 U.S.C. 154(b) by 144 days.

(21) Appl. No.: 10/663,449

(22) Filed: Sep. 16, 2003

(65) Prior Publication Data

US 2004/0053351 A1 Mar. 18, 2004

Related U.S. Application Data

(62) Division of application No. 09/697,934, filed on Oct. 27, 2000, now Pat. No. 6,743,596.

(51) Int. Cl.
*C12Q 1/56* (2006.01)
(52) U.S. Cl. ...................................................... 435/13
(58) Field of Classification Search .................. 435/13; 73/64.43; 422/73; 436/69; 600/369
See application file for complete search history.

(56) References Cited

U.S. PATENT DOCUMENTS

| | | | |
|---|---|---|---|
| 5,192,689 A | 3/1993 | Hemker et al. | |
| 5,292,664 A | 3/1994 | Fickenscher | |
| 5,443,960 A | 8/1995 | Dahlback | |
| 5,472,852 A | 12/1995 | Smirnov et al. | |
| 5,508,202 A | 4/1996 | Enomoto et al. | |
| 5,625,036 A | 4/1997 | Hawkins et al. | |
| 5,646,046 A | 7/1997 | Fischer et al. | |
| 5,716,795 A | 2/1998 | Matschiner | |
| 5,726,028 A | 3/1998 | Kraus | |
| 6,090,570 A | 7/2000 | Kraus | |
| 6,101,449 A | 8/2000 | Givens et al. | |
| 6,245,573 B1 | 6/2001 | Spillert | |
| 6,321,164 B1 * | 11/2001 | Braun et al. | 702/22 |
| 6,645,768 B1 * | 11/2003 | Tejidor et al. | 436/8 |
| 6,743,596 B1 * | 6/2004 | Fischer et al. | 435/13 |

FOREIGN PATENT DOCUMENTS

| | | | |
|---|---|---|---|
| CA | 2252983 | | 5/1999 |
| WO | WO 93/10261 | | 5/1993 |
| WO | WO 00/46603 | * | 8/2000 |

OTHER PUBLICATIONS

Cawthern, Kevin M., et al., "Blood coagulation in hemophilia A and hemophilia C," *Blood*, vol. 91, No. 12, Jun. 15, 1998, pp. 4581-4592.

Duchemin, Jerome, et al., " A New Assay Based on Thrombin Generation Inhibition to Detect Both Protein C and Protein S Deficiencies in Plasma", *Thrombosis and Haemostasis*, vol. 7, No. 3, pp. 331-338 (1994).

Mann, Kenneth G., "Biochemistry and Physiology of Blood Coagulation", *Thrombosis and Haemostasis*, vol. 82, No. 2, pp. 165-174 (1999).

Holmes, et al., "Novel, Bedside, Tissue-Factor-Dependent Clotting Assay Permits Improved Assessment of Combination Antithrombotic and Antiplatelet Therapy," *Circulation*, pp. 2051-2057, (Oct. 2000).

Rand, et al., "Blood Clotting in Minimally Altered Whole Blood," *Blood*, vol. 88, No. 9, pp. 3432-3445 (Nov. 1996).

International Search Report for International Applications Serial No. PCT/US01/32564 dated Apr. 25, 2002.

Supplementary Partial European Search Report for European Application No. 01983170.0 dated Sep. 26, 2005.

* cited by examiner

*Primary Examiner*—Ralph Gitomer
(74) *Attorney, Agent, or Firm*—Judith A. Roesler

(57) ABSTRACT

A method for assessing coagulation in a test sample is provided wherein an activator is added to a test sample in an amount sufficient to trigger a thrombin explosion dependent on propagation phase and amplification pathways but said amount insufficient to result in complete fibrin polymerization, followed by measuring the amount of fibrin polymerization due to the thrombin explosion and assessing the patient's coagulation based on the measurement of the fibrin polymerization. The method also provides a means for detecting defects in the propagation and amplification phases of coagulation.

16 Claims, 10 Drawing Sheets

METHOD FOR ASSESSING COAGULATION

CROSS-REFERENCE TO RELATED APPLICATIONS

This application is a divisional of U.S. application Ser. No. 09/697,934 filed on Oct. 27, 2000, now U.S. Pat. No. 6,743,596.

FIELD OF THE INVENTION

The present invention is related to U.S. Pat. No. 5,646,046 to Fischer et al and U.S. Pat. No. 6,101,449 to Givens et al, the subject matter of each being incorporated herein by reference. The invention is directed to a method for determining whether a patient is hypercoagulable, hypocoagulable or normal in a single test on a sample from the patient. The invention allows for globally assessing both the hypercoagulable potential and hypocoagulable potential of a patient in a single assay.

BACKGROUND OF THE INVENTION

Hemostasis is the entire physiological process of maintaining blood in a fluid state within intact blood vessels and preventing excess blood loss by arresting flow via the formation of a hemostatic plug. Normal hemostasis is maintained by tightly regulated interactions of the blood vessel wall, blood platelets and blood plasma proteins. Under normal conditions there is a delicate balance between the individual components of the hemostatic system. Any disturbances in this hemostatic balance, the hemostatic potential, could result in bleeding or thrombosis, FIG. 1. By "hemostatic potential" we mean the ability to maintain a balance between procoagulant and anticoagulant states, as measured by fibrin polymerization, when coagulation is initiated by a trigger or activator.

A thrombotic tendency (thrombophilia) results from the generation of excess thrombin activity and increased fibrin polymerization and clot formation (hypercoagulability) while a bleeding tendency (hemophilia) results from insufficient thrombin generation and reduced fibrin polymerization and clot formation (hypocoagulability). There is as yet no single laboratory parameter that is increased in all forms of hypercoagulability and decreased in all forms of hypocoagulability. This is in part due to factors other than plasma that play a part in hemostasis. As described above, these other factors include the blood vessel wall and platelets. However, large proportions of the hemostatic disorders are related to defects or deficiencies in the blood proteins that constitute the coagulation system. These proteins are responsible for the stabilization of the platelet plug by the formation of fibrin. Therefore, a global measure of the plasma contribution to coagulation would facilitate the investigation and management of patients with altered hemostasis.

Thrombophilia and haemophilia can be either congenital or acquired. The congenital forms have a genetic basis and are therefore not readily corrected. The acquired forms generally result from environmental changes, often the effect of drugs, and are therefore susceptible to manipulation. For example a normal individual given warfarin develops acquired haemophilia, stopping the warfarin abolishes the condition. A normal individual given high dose estrogen develops acquired thrombophilia, stopping the estrogen abolishes the condition. The fundamental basis of both the congenital (genetic) and acquired (environmental) thrombophilias and haemophilias is a change in either the amount or activity of one or more key components of the coagulation pathway. For example the most commonly recognized hereditary form of thrombophilia is a mutation in the factor V gene which results in the production of a structurally altered factor V protein (Factor V Leiden) that is resistant to enzymatic cleavage by protein C, a critical regulatory component. Classical Haemophilia A is due to a mutation in the factor VIII gene which results in either reduced production of factor VIII, or production of a structurally altered factor VIII protein that does not function correctly. In contrast to the congenital thrombophilias and haemophilias the acquired forms do not result from altered structure but rather alteration of the amount of a key component, typically more than one at a time. For example the thrombophilic effect of oestrogen is due to the composite effects of a rise in factors XI, IX, VIII, II and fibrinogen and a reduction in the anticoagulant protein S. The haemophilic effect of warfarin is due to a reduction in factors II, VII, IX and X. FIG. 2 illustrates the various states of coagulability and lists examples of assays used to assess the degree or presence of an imbalance. There is currently not an assay that can be used to assess both hyper and hypocoagulability simultaneously. This is due in part to the complexity of the coagulation process, the interdependence of the various components and the identification of a means to monitor the hemostatic potential of the entire coagulation system. FIG. 3 presents an overview of the coagulation process. The process can be divided into four dependent phases, (1) the initiation phase, (2) the propagation phase, (3) the amplification phase and (4) the polymerization phase. All of the phases are affected by regulatory and feedback processes referred to as anticoagulant pathways.

Initiation or triggering of coagulation occurs by exposure of tissue factor due to vascular damage, plaque rupture or monocyte expression as a result of inflammation. Trace amounts of FVIIa and tissue factor form the extrinsic Xase complex. This complex enhances the catalytic activity of VIIa towards factors X and IX resulting in the formation of the active enzymes Xa and IXa. Factor Xa generated by the extrinsic Xase complex forms a small amount of thrombin (IIa). The thrombin generated is capable of activating small amounts of the cofactors VIII and V. In vivo, the extrinsic Xase complex is quickly inactivated by Tissue Pathway Factor Inhibitor, TFPI, via the formation of a quaternary complex consisting of TF, VIIa and Xa. Under physiological conditions the extrinsic Xase generates only picomolar amounts of thrombin.

During the propagation phase of coagulation the role of the extrinsic Xase is minimized and Factor Xa is alternatively generated by the complex of the enzymes IXa and its cofactor VIIIa. This enzyme complex is referred to as intrinsic Xase. Formation of the Xa by the intrinsic Xase complex is approximately 50 fold more efficient than the extrinsic Xase. Factor Xa and its activated cofactor, FVa, form a complex on the surface of activated platelets. This is an efficient catalyst for the conversion of prothrombin to thrombin, referred to as the prothrombinase complex. Thrombin formed via the intrinsic Xase complex is capable of amplifying its own production by positive feedback (activation). Thrombin activates Factors VIII and V and Factor XI activation leads to further production of the enzymatic component of intrinsic Xase (Factor IXa). Normal thrombin production is highly regulated and localized. TFPI neutralizes the trigger for thrombin generation. Active proteases (IIa, Xa, IXa) must be inactivated by protease inhibitors to avoid disseminated thrombosis. One of the most significant of these inhibitors is antithrombin III (ATIII). Both thrombin and Xa, and to a lesser extent IXa released from membrane surfaces, are rapidly inhibited by ATIII. Thrombin can also bind non-damaged sub-endothelium via a receptor molecule, Thrombomodulin (TM). The formation of the IIa/TM complex changes the substrate specificity of thrombin from a procoagulant to an anticoagulant. Thrombin bound to TM is a potent activator of Protein C, converting it to the active enzyme Activated Protein C (APC). APC together with its cofactor protein S cleaves activated cofactors FVIIa and FVa yielding their inactive forms, FVIIIi and FVi. Thrombomodulin also accelerates the inactivation of thrombin by ATIII.

The formation of thrombin leads ultimately to cleavage of fibrinogen to form fibrin. During the polymerization phase cross-linking of soluble fibrin strands is mediated by Factor XIIIa, an enzyme generated by thrombin activation. The thrombin-TM complex activates the procarboxypeptidase thrombin activated fibrinolysis inhibitor (TAFI). Thus thrombin plays a role during this phase by both influencing the architecture and stabilization of the fibrin clot. Thrombin is a key enzyme and effector of the coagulation process. Thrombin is both a potent procoagulant and anticoagulant. However, it is thrombin's ability to cleave fibrinogen and its contribution to fibrin polymerization events that are critical to maintaining stasis.

Clot initiation, often referred to as clotting time, occurs at the intersection between the initiation and propagation phases when only approximately 5% of thrombin has been formed. The majority of the thrombin formed is generated after the initiation of fibrin polymerization, thus the rate of fibrin polymerization is a more sensitive indicator of the dynamics of coagulation. Changes in the propagation phase, amplification phase and anticoagulant pathways alter the rate of thrombin generation and the impact of thrombin availability on rate of fibrin polymerization. Recent studies by Cawthern et al. (1998) suggested that measurement of this thrombin is more informative than clotting time in assessing the pathophysiology of hemophilias. However these investigators measured thrombin by looking at the kinetics of formation of the thrombin-antithrombin complex (indictor of thrombin generation) and formation of fibrinopeptide A (indicator of fibrinogen cleavage) and not by measuring the kinetics of fibrin polymerization. Variations in concentration or quality of the fibrinogen or fibrin strands can only be measured as a function of the actual polymerization process. Assays currently used to assess variations in the coagulation process typically can only assess variations in one or two phases. These assays measure events independently and therefore negate or eliminate the ability to detect variations in the other phases or interactions between the various phases.

Assays associated with the assessment of bleeding risk include the Prothrombin Time (PT), Activated Partial Thromboplastin Time (aPTT), Thrombin Time (TT) and Fibrinogen (Fib) assays (FIG. 2). These assays are based on the addition of potent activators of the coagulation process and thus are only abnormal when major defects are present. These assays are not designed to detect the composite effect of multiple minor alterations. For example in the PT test, which utilizes a very high concentration of a tissue extract, called thromboplastin, and calcium are added to citrated plasma. Whole blood is mixed with citrate when the blood sample is taken. The citrate binds the calcium and "anticoagulates" the blood as calcium ions are required for assembly of the tenase and prothrombinase complexes. The blood sample is then centrifuged and the plasma is separated. When calcium is added back, the tenase (or Xase) and prothrombinase complexes can form and thrombin can be generated. The source of tissue factor is the thromboplastin. However, the concentration of tissue factor is extremely high (supraphysiological) and so only the initiation phase of thrombin generation is required. The propagation and amplification phases are bypassed. The prothrombin time is therefore insensitive to many changes in the coagulation pathway and is incapable of detecting hypercoaqulability. Assays based on diluted thromboplastin have been formulated to aid in the diagnosis of patients with antiphospholipid syndrome (APS). In these methods the thromboplastin together with the phospholipids are diluted to enhance the sensitivity of the PT to the presence of antiphospholipid antibodies. The dilute PT clotting time is prolonged in APS due the unavailability of phospholipid surfaces and therefore the assay is phospholipid dependent instead of TF dependent.

Assays associated with the assessment of a hypercoagulable state (FIG. 2) include the Thrombin Anti-Thrombin Complex (TAT), Prothrombin fragment F1.2, PAI 1, APCr and D-dimer. These assays are designed to measure a specific marker or product of the coagulation process. For example, the measurement of elevated levels of D-dimer indicates that the clotting process has been activated. However, there is no way of determining whether the D-dimer was being produced as a product of the normal healing process or if there is an underlying hypercoagulable risk. The hypercoagulable state cannot be globally assessed by a single assay but currently requires a battery of tests. A global assay for the assessment of hemostatic potential would be able to identify an imbalance utilizing a single assay principle that is sensitive to defects, singular or in combination. The assay would also be sensitive to effects of intervention to restore the hemostatic balance.

Recognising the limitations of the screening assays available for hypcoagulable assessment and the battery of assays required for hypercoagulable assessment, others have tried to develop global tests. These tests were designed to be sensitive to the amount of the biological components and their interactions, as well as measure the dynamics of thrombin generation including regulation. The thrombin generation curve was described more than 30 years ago as a measure of the thrombin generating potential of plasma. A modification of the thrombin generation curve has been described with quantification of thrombin with a exogenously added chromogenic substrate. This has been called the endogenous thrombin potential (ETP). The assay assumes that there is a direct correlation between endogenous thrombin potential measured via an exogenously added artificial substrate and the assessment of a hemostatic imbalance. The use of an artificial substrate instead of thrombin's natural substrate, fibrinogen, ignores the effects of variations in fibrinongen concentration and fibrinogen configuration. Thrombin is a cleavage product from the proteolysis of Prothrombin, a serine protease. Thrombin then cleaves fibrinogen, its natural substrate, resulting in soluble fibrin monomers that are crossed linked via FXIIIa to formed crossed linked polymerized clots. Thrombin is a highly regulated molecule that possesses both procoagulant and antithrombotic behavior. Additionally, there are numerous substrates that inactivate thrombin before it can cleave fibrinogen. In addition to not directly measuring the ability to form a clot the ETP assay has several other major limitations. Limitations of the test include:

1. The plasma sample must be defibrinated, typically with a snake venom. Defibrinating snake venoms activate FX and they also cleave the chromogenic substrate used to quantitate thrombin. This can cause a variable overestimate of the thrombin potential.

2 The plasma sample is considerably diluted in order to prolong the dynamics of thrombin generation. This results in a non-physiological regulation of the thrombin explosion.

3 The technique involves multiple subsampling at specified timepoints. For example, a computer linked pipeting device designed in order to terminate thrombin activity in the subsamples exactly at a specified time. It is possible to perform the assay manually but it is beyond the ability of many technologists and requires considerable skill. The test cannot be automated on standard clinical laboratory coagulometers.

4 The formation of thrombin-α2 macroglobulin complex leads to over-estimation of the thrombin potential. A complex mathematical manipulation of the results to approximate it to the true thrombin potential is therefore required.

5 Does not take into account the rate or ability of thrombin to cleave fibrinogen.

Duchemin et al. described a further modification of the ETP where the protein C pathway is assessed by adding exogenous thrombomodulin. This method was also modified to take into account proteins that modulate anticoagulant activity, including antithrombin III. Like ETP, this modified assay is designed to only measure thrombin generation and not the effects of thrombin, i.e. dynamic clot formation.

Other investigators have attempted to design assays sensitive to the composite of biological components of the coagulation process and their interactions. One such example is described by Kraus (Canadian application 2,252, 983). The method is however limited to determining the anticoagulant potential of a sample by adding thrombomodulin and thromboplastin in a coagulation test. In the described method the emphasis is on dilutions of thromboplastin such that thrombin is produced at a rate slow enough to enable sufficient activation of protein C during the measuring time of the coagulation apparatus. A disadvantage of this method is that because it depends on clot time, the amount of thromboplastin is more restrictive and higher concentrations are required to compensate for increases in clotting time when thrombomodulin is added. Because the method described is aimed at assessing anticoagulant potential and not global hemostatic potential the assay is not sensitive to defects in the propagation and amplification phases, the kinetics of clot polymerization or to the inter-relationships between the factors responsible for thrombin generation.

The present invention however assesses both the anticoagulant and procoagulant potential of a blood sample. Furthermore, the present invention's sensitivity can be enhanced by using more dilute coagulation activator, more dilute than has previously been used, since the endpoint method is not restricted to clot time but analysis can be conducted for the entire dynamic coagulation process as measured by evaluating kinetic parameters of the optical data profile. Analysis of more than simply clot time can be accomplished even when very weak and unstable clots are formed.

Variations in the amplification and/or propagation phases will reduce or alter the rate of generation of thrombin and thus impact the rate of fibrinogen cleavage and ultimately the rate of fibrin polymerization. Because the present invention can measure the rate of fibrin polymerization throughout the dynamic coagulation process, it measures the clinically important thrombin that is generated after clotting time.

Other prior art (Mann et. al.) assesses coagulation problems by taking a series of independent and indirect measurements. Thrombin generation is measured as a function of TAT complex formation or the use of a chromogenic substrate and the formation of fibrin as measured by the release of FPA. All of the systems and models to date have been designed to understand a discrete process or interaction of the coagulation process and cannot provide an assessment of the overall hemostatic potential. In contrast, the method of the present invention is designed to not only assess the interplay of the coagulation proteins together with synthetic cell surfaces, it is aimed at capturing this in a dynamic measurement that correlates to clinical outcome. The technology and methods described in the present invention can also be modified to introduce components of the fibrinolytic system as well as cells and flow conditions.

Givens et. al. demonstrated that a model which characterizes the process of clot formation and utilizes parameters in addition to clotting time is sensitive to defects in the clotting proteins. Table 1 describes the parameters defined by Givens et al. and FIGS. 4 and 5 illustrate how those parameters are determined and how they relate to fibrin polymerization for the PT and aPTT assays. However, this work was conducted utilizing data from the PT and APTT assays, which as discussed earlier, are only sensitive to events associated with the hypocoagulable state. Additionally, the work described was conducted in the presence of strong clot formation because of the addition of supraphysiological concentrations of tissue factor. Fibrin polymerization is significantly altered in a dilute systems designed for global hemostatic assessment resulting in weak and unstable clot formation. Global hemostatic assessment and new methods for monitoring and quantifying fibrin polymerization are required.

SUMMARY OF THE INVENTION

In order to overcome the deficiencies in the prior art as noted above, a global test of coagulation has now been developed, which is accurate and easy to use. With the present invention, a single test can be used to quantify both hyper- and hypocoagulability. The concept is based on the addition of a minimal concentration of coagulation activator sufficient to trigger but insufficient to result in complete fibrin polymerization so as to allow detection of perturbances in the propagation, amplification and polymerization pathways. In a dilute system, the coagulability (hyper/hypo) of a sample determines the magnitude of the thrombin explosion and the direct and indirect influence that has on the rate of fibrin polymerization. This concept is contrary to an assay system such as the PT, which uses excess amounts of TF (or thromboplastin). In the method of the present invention, therefore, disturbances in the propagation and amplification loops are accessible, whereas in the traditional PT test, these parts of the coagulation pathway are overshadowed by the excessive amounts of Factor IIa produced by the initiation phase.

In one embodiment of the invention, the rate of fibrin polymerization produced by a standardized coagulation activator dilution is then used to indicate if a plasma sample is normal, hyper- or hypocoagulable. In addition, the technique can be used to determine how much the plasma needs to be modified in order to restore coagulability to normal. For example, in the case of hypocoagulability, this might be achieved by clotting factor replacement or in the case of hypercoagulability, by the addition of a natural anticoagulant or the use of an anticoagulant drug.

In the present invention, at a given coagulation activator dilution, the rate of fibrin polymerization of haemophilia plasmas are less than the rate of polymerization for a normal plasma and the rate of fibrin polymerization of thrombophilia plasmas are greater than that of a normal sample. The rate of fibrin polymerization is sensitive to minor changes in the components of hemostasis even when differences in clotting time cannot be detected. FIG. 6 illustrates waveforms from the normal, hypercoagulable and hypocoagulable specimens. The rate of polymerization is affected even though the time of clot initiation is essentially unchanged.

In another embodiment of the present invention, a test is provided that can be used to determine the degree of hyper- or hypocoagulability of a plasma sample. Furthermore, it can be used on samples containing platelets or other cells as a measure of the contribution of cellular components to coagulability. The test, in some embodiments, relies on the use of a standardized dilution of thromboplastin in the presence of an excess of phospholipids with the rate of fibrin formation as the detection endpoint. The test is simple and can be automated on standard laboratory coagulometers. The test in the present invention can be run on a test sample in the absence of the addition of an exogenous substrate, e.g. a chromogenic substrate. The test is sensitive to fibrin concentration and/or configuration.

In a further embodiment of the invention modifications to the components or concentrations of the reagent or endpoint selection are tailored to facilitate the development and/or monitoring of novel pharmaceutical agents. Examples of such applications are inhibitors of initiation of the TF pathway (TFPI, FVIIa inhibitors), inhibitors of thrombin generation such as inhibitors of FXa, (synthetic pentasaccharides) and inhibitors of thrombin activity (direct thrombin inhibitors). Lipid composition, size or concentration can also be modified to tailor the assay towards the development of drugs targeted to the propagation and amplification pathways. For example, lipid composition can be altered to produce vesicles that maximize Xa generation or alternatively, designed to maximize prothrombinase activity. Thus the efficacy of inhibitors of Xa and those directed at the prothrombinase complex may be assessed. The invention can also be modified to focus on the anticoagulant potential of the plasma by including thrombomodulin, an activator of protein C. Lipid vesicles maximizing the activity of APC could also be added to the reagent. The assay can also be modified to exaggerate a mildly abnormal subpopulation. The consequences of this approach are that severely thrombotic or hemorrhagic samples will exceed the signal to noise ratio and not be measured but subtle differences at the onset of a disease or an earlier indication of effective intervention would be gained. Endpoint selection and ratios derived from comparison to known samples would be exploited to further improve sensitivity and specificity of the reagent modifications. These approaches would therefore be utilized in the drug discovery and drug development processes where assay designed for a global assessment of the hemostatic potential are required.

Figure 1:
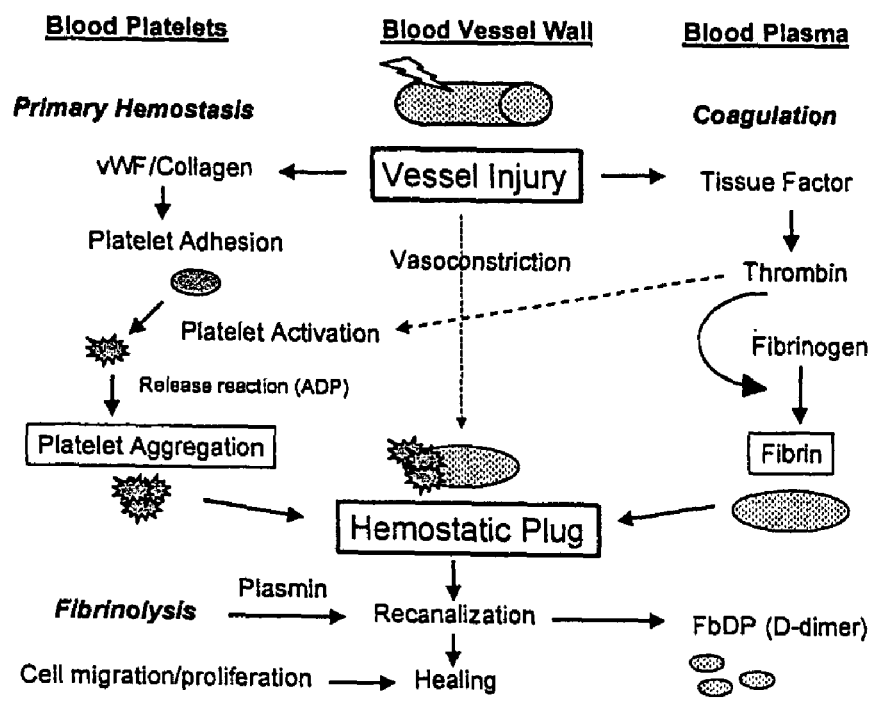
FIG. 1 illustrates the consequences of any disturbance in this so-called hemostatic balance or potential.

Abbreviations in the figures are as follows:
Activated Factor IX (FIXa)
Activated Factor V (FVva)
Activated Factor VII (FVIIa)
Activated Factor VIII (FVIIa)
Activated Factor X (FXa)
Activated Factor XI (FXIa)
Activated Factor XIII (FXIIIa)
Activated Protein C (APC)
Factor II (FII)
Factor IX (FIX or F9)
Factor V (FV)
Factor V Leiden (FVL)
Factor VII (FVII)
Factor VIII (FVIII or F8)
Factor VIII Deficient (FVIII-def)
Factor X (FX)
Factor XI (FXI)
Factor XIII (FXIII)
George King (GK)
HRF (Hemophilia Research Foundation)
Organon Teknika Normal Pool Plasma (OT NPP)
Protein C (PC)
Protein C Deficient (PC Def.)
Protein S (PS)
Protein S Deficient (PS-Def)
Prothrombin Mutation 20210 (PT 20210)
Recombinant Tissue Factor (rTF)
Thrombin or aActivated Factor II (FIIa)
Thrombomodulin (TM)
Tissue Factor (TF)
Von Willebrand Factor (vWF)

DETAILED DESCRIPTION OF THE PREFERRED EMBODIMENT

The present invention is directed to a method for determining if a patient or specimen from said patent is hypercoagulable, hypocoagulable or normal in a single test, and comprises the steps of initiating coagulation in a patient's sample in vitro in the presence of an activator. Said activator is added to the sample in an amount which will result in intrinsic tenase-dependent fibrin polymerization (involves propagation and amplification loops). Preferably the plasma sample is undiluted thus allowing for sufficient concentrations of all of the endogenous proteases and inhibitors. Formation of the fibrin polymerization is recorded over time so as to derive a graphic time-dependent polymerization profile. This profile will show whether the patient is hypercoagulable, normal, or hypocoagulable by comparing the sample profile with a profile from a known sample.

Preferably, the activator is a thromboplastin, more preferably Tissue Factor (TF). In its most preferred form, the TF is recombinant TF (rTF) that is relipidated with phospholipids, which form liposome vesicles. Preferably phospholipids provide the surfaces to assemble intrinsic Xase and prothrombinase complexes. The phospholipids are present at a concentration, which is not rate limiting to the coagulation process and remains constant and independent of dilution. These phospholipid vesicles mimic platelet and monocyte surfaces.

Optical data profiles are generated on an automated coagulation analyzer such as the MDA™ 180 offered by Organon Teknika Corporation. Preferably endpoints such as the time of clot initiation and the rate of polymerization are calculated from the data profiles. More preferably the $1^{st}$ and $2^{nd}$ derivatives from the data profile are calculated and the min and max of the derivatives are calculated with respect to value and the associated time index. Most preferably the endpoints are calculated and one or more of the following ratios are calculated using the mentioned endpoints:

Option 1—Endpoint(s)
Option 2—Ratio at different dilutions (ratio 1)
Endpoint (z) for dilution (x)
Endpoint (z) for dilution (y)
Option 3—Ratio of dilutions compared to normal (ratio 2)
Ratio 1 for patient sample
Ratio 1 for normal plasma
Option 4—Ratio for different reagent formulations
Ratio 2 with formulation (a)
Ratio 2 with formulation (b)
Option 5—Ratio of different endpoints
Ratio 2 with endpoint (z)
Ratio 2 with endpoint (z')
Option 6—Ratio of specimen to normal at a given dilution
Endpoint (z) at dilution x for a specimen
Endpoint (z) at dilution x for a normal plasma Additionally, other ratios, differences or models to normalize the assay can be calculated. The normal plasma can be substituted with any known plasma. Known plasma is defined as a plasma that has been characterized with respect to a condition of the specimen.

FIG. 1 illustrates the consequences of any disturbance in this so-called hemostatic balance or potential. Too little hemostasis (decreased platelet function, hypo-coagulation, hyper-fibrinolysis) at the site of injury leads to persistent bleeding, while too much hemostasis (increased platelet function, hyper-coagulation, hypo-fibrinolysis) leads to the formation of an excessive thrombus with vascular obstruction and ischemia.

Figure 2:
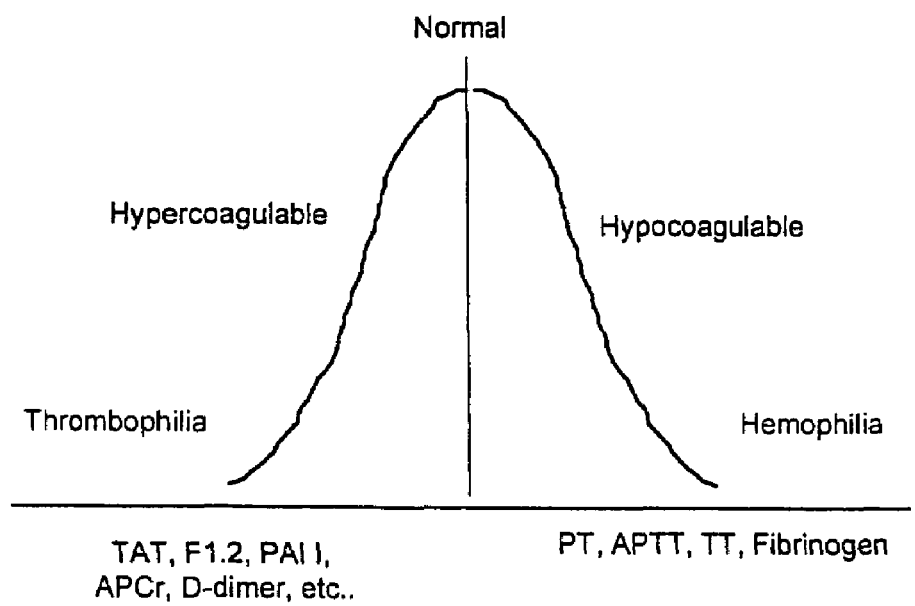
FIG. 2 illustrates the conditions associated with being out of hemostasis and lists examples of assays used to assess the degree or presence of an imbalance.

FIG. 2 illustrates the conditions associated with being out of hemostasis and lists examples of assays used to assess the degree or presence of an imbalance.

Figure 3:
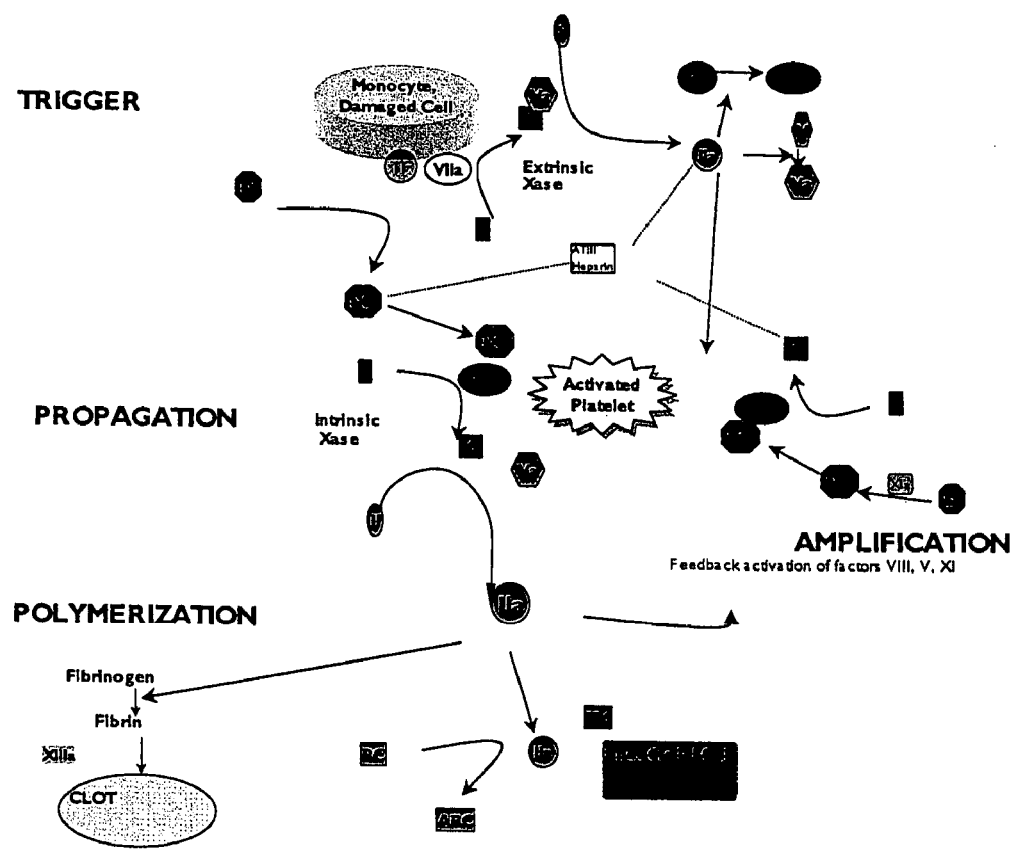
FIG. 3 illustrates the four dependent phases of the coagulation process.

FIG. 3 illustrates the four dependent phases of the coagulation process, (1) the initiation phase, (2) the amplification phase, (3) the propagation phase and (4) the polymerization phase of hemostasis. All of the phases are affected by regulation and feedback processes referred to as anticoagulant pathways.

Figure 4:
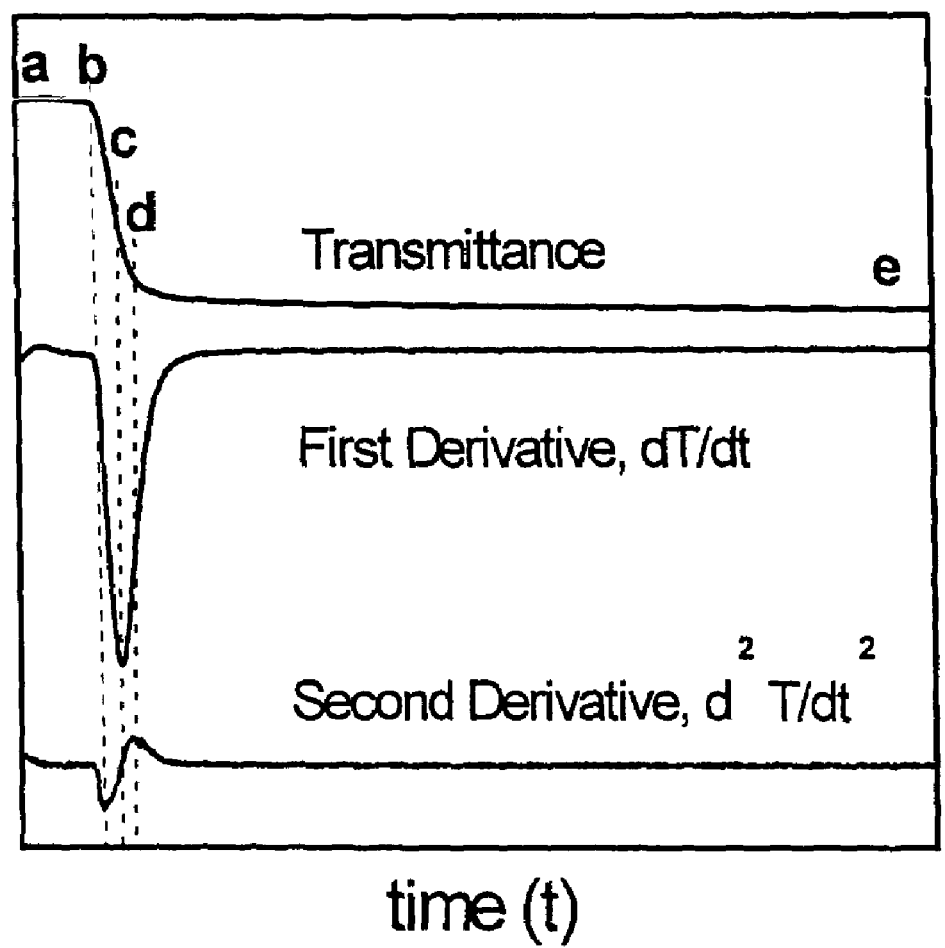
FIG. 4 illustrates the optical data from a clotting assay and the first and second derivative calculated from that data.

FIG. 4 illustrates the optical data from a clotting assay and the first and second derivative calculated from that data. Table 1 describes a set of parameters calculated from the data and derivatives illustrated in FIG. 4.

TABLE 1

| Parameter | Description |
| --- | --- |
| Slope 1 | Initial slope from point A to point B |
| Delta 1 | Amplitude of signal change from point A to point B |
| Slope 3 | Final slope from point D to point E |
| Delta | Amplitude of signal change |
| Index Min 1 | Time at point C |
| Min 1 | Minimum value of 1st derivative (Rate of change at point C) |
| Index Max 2 | Time at point D |
| Max 2 | Max. value of 2nd derivative (Acceleration at point D) |
| Index Min 2 | Time at point B |
| Min 2 | Minimum value of 2nd derivative |

Figure 5:
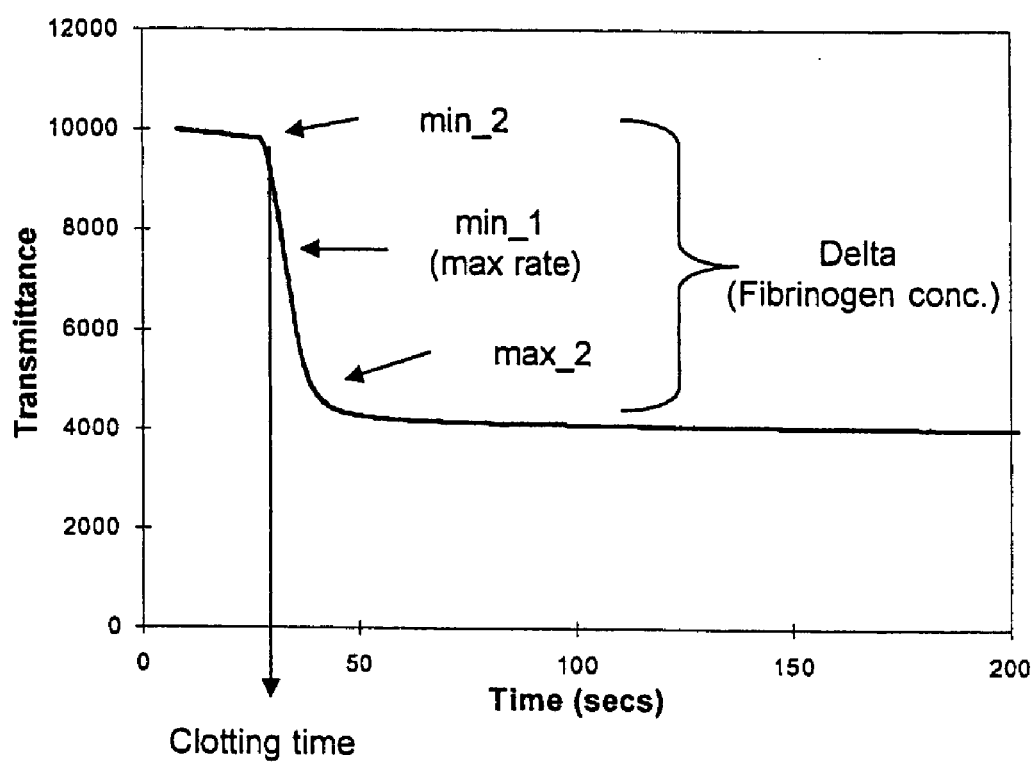
FIG. 5 illustrates where min__2, the time index of min2 (clotting time), min__1, max__2 and delta (proportional to fibrinogen concentration) are located in the optical data profile.

FIG. 5 illustrates where min_2, the time index of min2 (clotting time), min_1, max_2 and delta (proportional to fibrinogen concentration) are located in the optical data profile.

Figure 6:
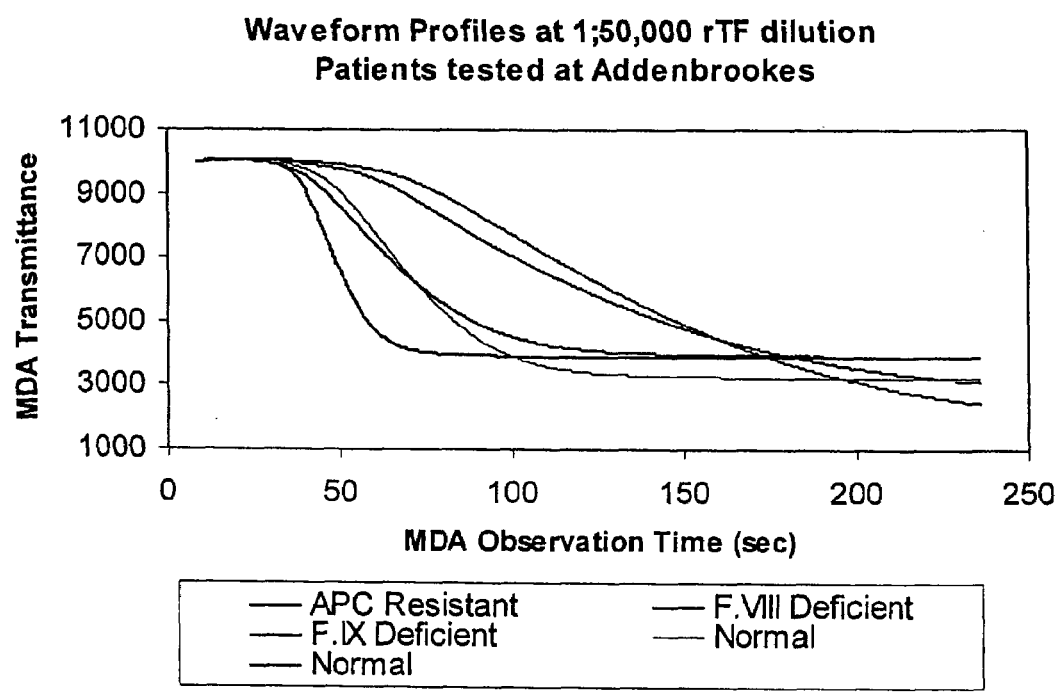
FIG. 6 illustrates examples of waveforms for the global screening assay at dilute tissue factor.

FIG. 6 contains examples of waveforms for the global screening assay at dilute tissue factor. The APC resistant, , hypercoagulable specimen, generates a waveform that has essentially the same time of clot initiation compared to the normal. However, the rate of fibrin polymerization for the hypercoagulable specimen is significantly greater than that of the normal. The FVIII and FIX deficient hypocoagulable specimens, have only a slightly prolonged time of clot initiation whereas the rates of polymerization are significantly reduced when compared to normal or hypercoagulable specimens.

Figure 7:
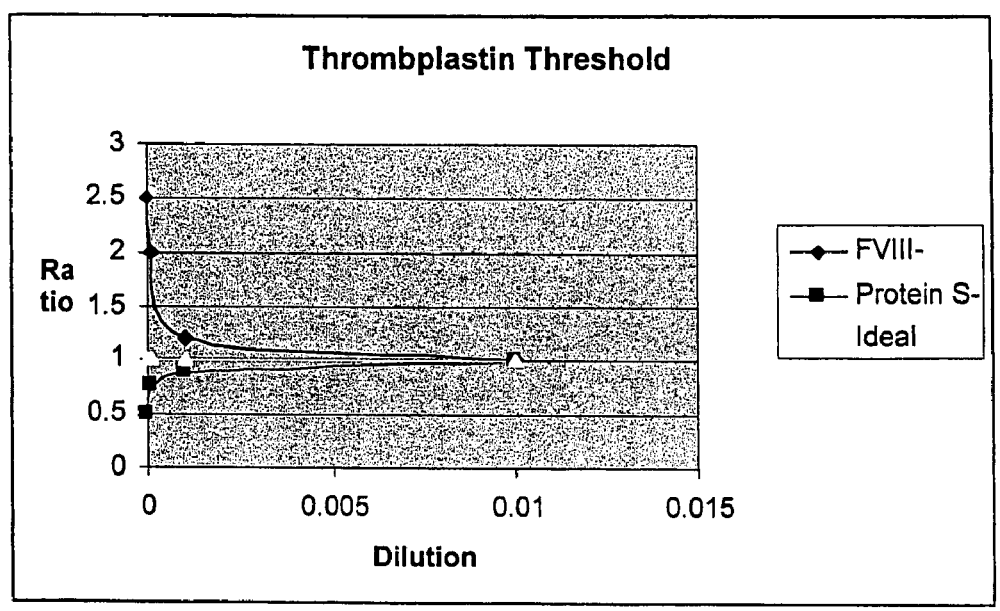
FIG. 7 illustrates the change in ratio as a function of dilution for a FVIII deficient specimen and a Protein S deficient Specimen.

FIG. 7 illustrates the change in ratio as a function of dilution for a FVIII deficient specimen and a Protein S deficient Specimen. The ratio values at 1:50,000 dilution of thromboplastin deviate from the response of the normal plasma. The hypocoagulabe specimen produces ratios that are greater than 1 and the hypercoagulable specimen has ratios that are less than 1 for this endpoint (clot time)/ratio combination. Additionally, the abnormal specimen deviates from normal at different dilutions and in opposite directions.

Figure 8:
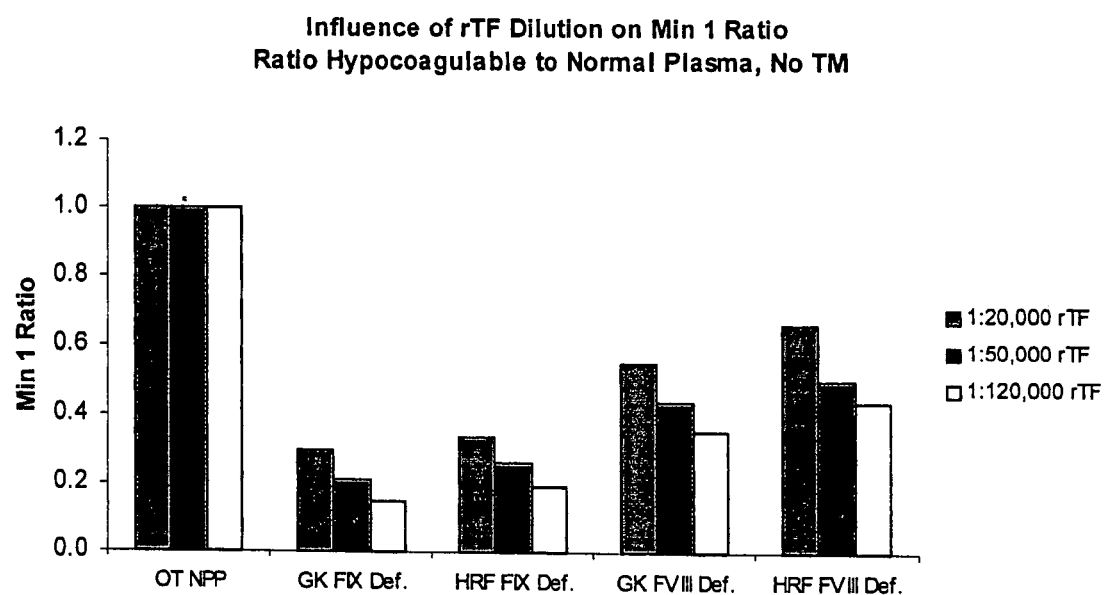
FIG. 8 illustrates ratios of the min-1 values (the maximum rate of fibrin polymerization) for hypocoagulable specimens at three dilutions of rTF compared to the min__1 values of the ratio of the same dilution of a normal plasma.

FIG. 8 contains ratios of the min-1 values (the maximum rate of fibrin polymerization) for hypocoagulable specimens at three dilutions of rTF compared to the min_1 values of the ratio of the same dilution of a normal plasma. All of the ratios of the hypocoagulable plasmas for all three dilutions are less than the normal response (values of <1). As the dilution increase, i.e. less tissue factor is provided, the difference in the ratios increases.

Figure 9:
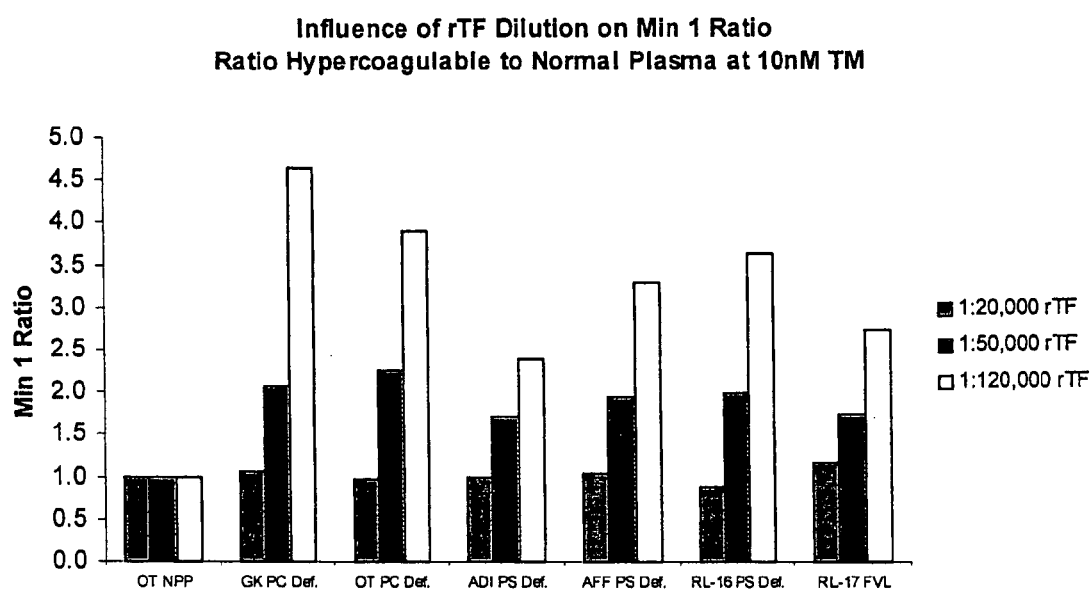
FIG. 9 illustrates ratios of the min__1 values for hypercoagulable specimens at three dilutions of rTF and 10 nM thrombomodulin compared to min__1 values of the ratio for the same conditions of a normal plasma.

FIG. 9 illustrates ratios of the min_1 values for hypercoagulable specimens at three dilutions of rTF and 10 nM thrombomodulin compared to min_1 values of the ratio for the same conditions of a normal plasma. All of the ratios of the hypercoagulable plasmas for all three dilutions are greater than the normal response (values of >1). As the dilution increase, i.e. less tissue factor is provided, the difference in the ratios increases.

Figure 10:
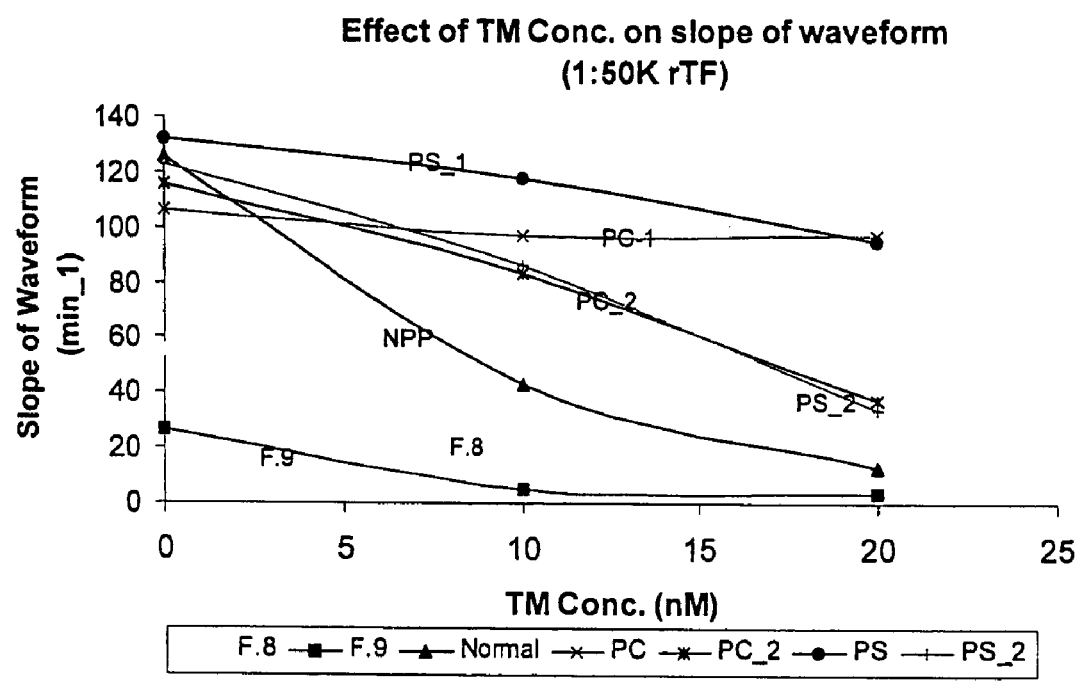
FIG. 10 illustrates the effects on min__1 values of varying tissue factor and thrombomodulin concentrations on results for hypercoagulable, hypocoagulable and normal plasmas.

FIG. 10 illustrates the effects on min_1 values of varying tissue factor and thrombomodulin concentrations on results for hypercoagulable, hypcoagulable and normal plasmas.

The data indicate that an optimal concentration can be defined to facilitate differentiation between normal, hypercoagulable and hypocoagulable plasmas. Additionally, other concentrations of tissue factor and thrombomodulin facilitate improvements in sensitivity and specificity for a particular condition at the expense of the sensitivity and specificity of another type of condition.

Tables 2 and 3 summarize the results of measuring the kinetic parameters, min 1 and min 2 with a series of defined patient plasmas. The concentration of TF was 10 μM and TM was adjusted to 10 nM. The phospholipid concentration was kept constant at 150 micromolar. The data shows that the reagent in the presence of TM is able to differentiate hyper and hypocoagulable plasmas with a single reagent formulation. Additionally, the data indicates that TM is not essential to obtain discrimination between the hypocoagulable and a normal standard plasma pool. Data are calculated as ratios to a normal pool with and without thrombomodulin. Ratios of the min2 parameter were higher than the corresponding min1 values for the hypercoagulable plasmas.

Tables 2 and 3 illustrate the behavior of defined plasmas in the presence and absence of thrombomodulin as determined by the kinetic endpoints min_1 and min_2.

points were calculated for time and rate indices of clot formation. Ratios of the endpoints were compared to other dilutions and other samples as follows:

$$\text{Ratio} = \frac{\text{endpoint of reagent } diln\ (x) \text{ for Specimen/endpoint of reagent } diln\ (y) \text{ for specimen}}{\text{endpoint of reagent } diln\ (x) \text{ for } npp / \text{endpoint of reagent } diln\ (y) \text{ for } npp}$$

Where x is a 1:100 dilution and y is a series of dilutions

As the dilution of the reagent become greater (y becomes larger) the results for the two abnormal plasmas (the aforementioned hypercoagulabe and hypocoagulable plasmas) tested began to deviate from the calculated endpoints or ratios of the normal plasma. The results can be expressed as the magnitude of deviation at a given dilution or as the dilution required to deviate from ideal (normal value or normal range). FIG. 7 illustrates that the hypercoagulable and hypocoagulable results deviate in opposite directions indicating the ability to differentiate between the two conditions.

TABLE 2

| Plasma Type | Min_1 values with no TM | Min_1 values with 10 nM TM | Min_1 Ratio Specimen without TM/Normal plasma without TM | Min_1 Ratio Specimen with 10 nM TM/Normal plasma with 10 nM TM |
| --- | --- | --- | --- | --- |
| Normal Plasma | 101 | 68 | | |
| PC Deficient | 110 | 105 | 1.09 | 1.54 |
| Lupus | 116 | 79 | 1.15 | 1.16 |
| FV Leiden | 95 | 77 | 0.94 | 1.13 |
| FV Leiden & PT 20210 | 260 | 248 | 2.57 | 3.64 |
| FIX Deficient | 71 | 40 | 0.70 | 0.59 |
| FVIII Deficient | 84 | 46 | 0.83 | 0.68 |

TABLE 3

| Plasma Type | Min_2 values with no TM | Min_2 values with 10 nM TM | Min_2 Ratio Specimen without TM/Normal plasma without TM | Min_2 Ratio Specimen with 10 nM TM/Normal plasma with 10 nM TM |
| --- | --- | --- | --- | --- |
| Normal Plasma | 34.8 | 11.9 | | |
| PC Deficient | 36.4 | 27.6 | 1.05 | 2.32 |
| Lupus | 47.4 | 23.6 | 1.36 | 1.98 |
| FV Leiden | 32.6 | 20.3 | 0.94 | 1.71 |
| FV Leiden & PT 20210 | 181 | 165 | 5.2 | 13.9 |
| FIX Deficient | 21 | 9 | 0.60 | 0.76 |
| FVIII Deficient | 16.4 | 6.4 | 0.47 | 0.54 |

EXAMPLE 1

The assay was conducted by adding 50 uL of plasma to 50 uL of the activator and then adding 50 uL of the start reagent. A normal sample, a hypocoagulable sample (Factor VIII deficient plasma) and a hypercoagulable plasma (protein S deficient plasma) were evaluated at various dilutions of the activator. The activator was a commercially available thromboplastin (Thromborel R, Behring Diagnostics) diluted with a buffer at two dilutions, a 1:100 and 1:50000 of its original concentration. The start reagent consisted of 0.25 M Calcium Chloride. The assay was conducted at 37 C and the reaction was monitored at 580 nm for 300 seconds. End-

EXAMPLE II

The assay was conducted by adding 50 uL of plasma to 50 uL of the activator and then adding 50 uL of the start reagent. A set of normal samples, a series of samples from hypocoagulable individuals and a series of plasmas from hypercoagulable individuals were evaluated at various dilutions of the activator. The activator was a preparation of TF reconstituted with phospholipids to between 20 to 3.3 pM (1:20,000 to 1:120,000 dilution) and phospholipid prepared by extrusion with and without TM. The start reagent consisted of 0.025 M Calcium Chloride. The assay was conducted at 37 C and the reaction was monitored at 580 nm for 300 seconds. The value of the minimum of the $1^{st}$ derivative and the value of the minimum of the $2^{nd}$ derivative were calculated for all samples. Ratios of the endpoints were compared to other dilutions and other samples as follows:

Option 1—Endpoint(s)
Option 2—Ratio at different dilutions (ratio 1)

$$\frac{\text{Endpoint }(z)\text{ for dilution }(x)}{\text{Endpoint }(z)\text{ for dilution }(y)}$$

Option 3—Ratio of dilutions compared to normal (ratio 2)

$$\frac{\text{Ratio 1 for patient sample}}{\text{Ratio 1 for normal plasma}}$$

Option 4—Ratio for different reagent formulations $$\frac{\text{Ratio 2 with formulation }(a)}{\text{Ratio 2 with formulation }(b)}$$

Option 5—Ratio of specimen to normal at a given dilution $$\frac{\text{Endpoint }(z)\text{ at dilution }x\text{ for a specimen}}{\text{Endpoint }(z)\text{ at dilution }x\text{ for a normal plasma}}$$

FIGS. 8 and 9 illustrate the differentiation for hypercoagulable and hypercoagulable specimens when compared to normal. Tables 2 and 3 illustrate the behavior of defined plasmas in the presence and absence of thrombomodulin as determined by the kinetic endpoints min_1 and min_2. FIG. 10 demonstrates the effect of varying tissue factor and thrombomodulin on the results from hypercoagulable, hypercoagulable and normal plasmas. The data indicate that variations in the concentrations facilitate improvements in sensitivity and specificity for a condition at the expense of the sensitivity and specificity of another type of condition.

In one preferred embodiment, the TF is added to the sample at a concentration of about less than or equal to 10 picomolar and the phospholipid concentration of between 10 to 300 µM. The TF can be added to the sample at a concentration of 3 to 10 picomolar and the phospholipid vesicles can be added at 100 to 150 micromolar. Preferably thrombomodulin is added at 0 to 30 nanomolar and most preferably at a concentration of 5 to 15 nanomolar. Calcium Chloride is most preferably added at a concentration of about 25 mM. All of the reagent component concentrations described are further diluted 1:3 in the plasma/buffer matrix in the cuvette.

One or more parts or endpoints of the time dependent measurement profile obtained by monitoring fibrin polymerization in the test sample can be compared to the same parts or endpoints of a time dependent measurement profile obtained by monitoring fibrin polymerization in the test sample at a different coagulation activator concentration and/or to the same parts or endpoints for a known (e.g. normal) test sample. The part of the profile can be one or more of initiation of clot formation, overall change in profile, slope of profile after initiation of clot formation, and acceleration at the time of clot initiation. Also, if at least two time-dependent fibrin polymerization profiles are obtained, an additional profile can be obtained for a known sample from computer memory or by adding the activator at at least one concentration to a known sample and monitoring the formation of fibrin polymerization over time. The parameter from each time-dependent fibrin polymerization profile having varying activator concentrations can be determined and a concentration at which the at least one parameter of said sample being tested deviates from normal can be determined. The point of deviation is indicative of the hypercoagulable or hypocoagulable state. The part of the profile is preferably a time index of the minimum of the first derivative, the value of the minimum of the first derivative, the time index for the minimum of the second derivative, the value for the minimum of the second derivative, the time index of the maximum of the second derivative, the value of the maximum of the second derivative, or the overall magnitude of change. More preferably, the part is rate or acceleration of fibrin polymerization, wherein the rate or acceleration is compared to rate or acceleration at the same activator concentration for the known sample.

Though endpoints can be directly compared as noted above, a difference or ratio of said parameters for said test sample and said normal sample can instead be determined. If the parameter is clot time, a ratio of clot times at different activator concentrations can be determined. A ratio of other parameters, rate of clot formation, maximum acceleration of clot formation, turbidity at a predetermined time period, and total change in turbidity can also be determined in order to measure defects in the thrombin propagation and/or amplification phases. Also, a ratio can be taken of the at least one parameter for said test sample to the same parameter for a normal sample. And, the ratio can be determined for multiple concentrations of activator to better characterize the hypo- or hyper-coagulability. For example, the concentration at which said ratio (test sample/known sample) departs from 1 (or a range around 1) can show the abnormal coagulability.

Other ratios aid determination of the hemostatic potential (e.g. the hypocoagulability, stasis, or hypercoagulability; or the bleeding or thrombotic tendency of the patient). For example, a first ratio can be calculated for the at least one parameter at two different concentrations of the activator. A second ratio can be calculated of said first ratio at the two different activator concentrations relative to a first ratio calculated for a known sample at two different activator concentrations. A third ratio can be calculated of the second ratio at a first reagent formulation and the second ratio at a second reagent formulation. Though the second reagent can vary in a number of ways from the first, in one embodiment the first reagent formulation can comprise a coagulation activator and the second reagent formulation can comprise a coagulation activator and an activator of an anticoagulant pathway. A fourth ratio could be calculated of the second ratio calculated for one endpoint relative to the second ratio calculated for a different endpoint. Significant information can be obtained by changing the reagent formulation and comparing the same endpoints, or by maintaining the reagent formulation (though possibly at a different concentration) and comparing different endpoints (or both endpoint and reagent formulation and/or concentration can be altered).

An activator of one or more anticoagulant pathways can be added along with the coagulation activator. Such an additional activator can be any activator of an anticoagulant pathway, such as the protein C pathway. Thrombomodulin is one example, which can be added in the form of purified human thrombomodulin, purified non-human mammalian thrombomodulin, soluble or membrane associated thrombomodulin, native thrombomodulin or reconstituted with phospholipids, partially or fully glycolsylated thrombomodulin, or fully deglycosylated thrombomodulin, with added heparin-like molecules. The coagulation activator can be any suitable activator including recombinant or purified tissue factor, truncated tissue factor, or cells expressing tissue factor on their surface. If vesicles or liposomes are added, they can be in the form of platelets, cellular debris, phospholipids or platelet microparticles. A metal salt if added can be a halide of magnesium, calcium or manganese, or other divalent metal salt. Buffers and stabilizers could also be added if desired.

A reagent or kit for assessing hemostatic potential should have a coagulation activator. Additional components of the reagent or kit could include the above-mentioned vesicles, metal salt or ions, and anticoagulant pathway activator, if desired. In the kit, the components could all be provided in separate containers, or mixed together in any combinations in one or more containers. If phospholipid vesicles are added, they can be any suitable phospholipid or combination of phospholipids including one or more of phosphatidylcholine, phosphatidylethanolamine and phosphatidylserine, which can be provided at a ratio of approximately 5 to 30 mole percent phosphatidylethanolamine, 1 to 10 percent phosphatidylserine and the remainder phosphatidylcholine. These vesicles can be prepared in a variety of ways to yield liposomes of various sizes. Phospholipids can be provided at a concentration that is not rate limiting, e.g. at a concentration of from 10 to 300 micromolar, and preferably in the range of from 50 to 200 micromolar. Tissue factor can be provided at a concentration of 10 picomolar or less, 8 picomolar or less, or preferably 6 picomolar or less. The concentration could be 3 picomolar or less, though whatever concentration of tissue factor, it should allow for hemostatic potential assessment as set forth herein. If it is desired to add thrombomodulin, it can be provided at a concentration of 30 nanomolars or less, preferably in a range of from 5 to 20 nanomolar. If a metal salt is to be added, it can be provided in a reagent or kit at a concentration of from 5 to 50 mM, preferably from 15 to 35 mM.

Variations to the above described method, kit and reagent are possible, and the embodiments disclosed herein should be considered illustrative and not limiting.

We claim:

1. A method for determining both hypercoagulability and hypocoagulability in a test sample, comprising:
   (a) providing a sample;
   (b) adding an activator to said sample in an amount sufficient to trigger a thrombin explosion dependent on propagation phase and amplification loops and subject to one or more anticoagulant pathways but said amount insufficient to result in complete fibrin polymerization;
   (c) measuring the amount of said fibrin polymerization due to said thrombin explosion; and
   (d) assessing both hypercoagulability and hypocoagulability in said test sample based on said measured fibrin polymerization.

2. The method of claim 1, wherein the activator of is added to said test sample to cause the fibrin polymerization to be sensitive to the protein C pathway, and said activator is selected from the group consisting of purified human thrombomodulin, purified non-human mammalian thrombomodulin, soluble or membrane associated thrombomodulin, native thrombomodulin or thrombomodulin reconstituted with phospholipids, partially or fully glycolsylated thrombomodulin, fully deglycosylated thrombomodulin, and combinations thereof.

3. The method of claim 1, wherein the activator comprises recombinant or purified tissue factor, truncated tissue factor, or cells expressing tissue factor on their surface, and step (b) further comprises adding to said test sample one or more vesicles selected from the group consisting of platelets, cellular debris, phospholipid vesicles, platelet microparticles, and combinations thereof.

4. The method of claim 1, wherein the fibrin polymerization is monitored over time to provide a time-dependent measurement profile.

5. The method of claim 4, wherein an endpoint is extracted from the time-dependent measurement profile.

6. The method of claim 5, wherein the endpoint is normalized by using a model.

7. The method of claim 6, wherein the model is a ratio or difference of the endpoint compared to an endpoint from a time-dependent measurement profile for a known sample.

8. The method according to claim 4, wherein a rate or an acceleration of fibrin polymerization is determined from the time-dependent measurement profile, wherein said rate or said acceleration is compared to a known rate or a known acceleration at a same activator concentration for a known sample and/or the rate or acceleration of the test sample at a different activator concentration.

9. A method for detecting defects in a propagation and/or an amplification phase in a coagulation system of a test sample, comprising:
   (a) providing a sample to determine both hypercoagulability and hypocoagulability to be tested;
   (b) adding an activator in an amount sufficient to trigger a thrombin explosion that is dependent on the propagation phase and/or amplification loops of the coagulation system in the test sample but said amount insufficient to result in complete fibrin polymerization;
   (c) measuring said fibrin polymerization; and
   (d) detecting defects of regulation or modulation in the propagation phase and/or amplification loops in the coagulation system of the test sample based on the measured fibrin to determine both hypercoagulability and hypocoagulability polymerization.

10. The method according to claim 9, wherein the fibrin polymerization is monitored over time to provide a time-dependent measurement profile and all or part of said time-dependent profile of said sample to be tested is compared to all or part of a time-dependent profile for a known sample.

11. The method according to claim 10, wherein part of a fibrin polymerization profile of said test sample is compared to a same part of a profile for a known sample.

12. The method according to claim 11, wherein said part is rate or acceleration of fibrin polymerization of said test sample, wherein said rate or acceleration is compared to rate or acceleration at the same activator concentration for said known sample.

13. The method according to claim 9, wherein one or more parameters of said time-dependent fibrin polymerization profile are compared to the same one or more parameters for a normal sample, in order to determine whether said patient is hypercoagulable, normal or hypocoagulable.

14. The method according to claim 13, wherein at least one parameter of said time-dependent fibrin polymerization profile includes at least one or more of the group consisting of time of initiation of clot formation, rate of clot formation, maximum acceleration of clot formation, turbidity at a predetermined time period, and total change in turbidity.

15. The method according to claim 14 wherein said one or more parameters are measures of defects in the thrombin propagation and/or amplification phases.

16. The method according to claim 14, wherein a ratio of said at least one parameter for said test sample to the same parameter for a normal sample is determined.

* * * * *